United States Patent [19]

Liao et al.

[11] 4,382,075

[45] May 3, 1983

[54] STABILIZED ROMANOWSKY STAIN SOLUTION

[75] Inventors: John C. Liao, Elkhart; John L. Ponzo, Mishawaka; Ellen M. Jenning, South Bend, all of Ind.

[73] Assignee: Miles Laboratories, Inc., Elkhart, Ind.

[21] Appl. No.: 250,732

[22] Filed: Apr. 3, 1981

[51] Int. Cl.$^3$ .................. G01N 1/30; C09B 67/00; C09B 67/18
[52] U.S. Cl. .................................. 424/3; 8/506; 8/638; 8/644; 8/657
[58] Field of Search ............... 8/506, 638, 644, 657; 424/3

[56] References Cited

U.S. PATENT DOCUMENTS 4,290,769 9/1981 Liao ........................... 8/506

OTHER PUBLICATIONS

Dean, Stain Technology, vol. 52, 1977, pp. 35–46.
Gilliland et al., Stain Technology, vol. 54, No. 3, pp. 141–150.

Primary Examiner—Anna P. Fagelson
Attorney, Agent, or Firm—Jerome L. Jeffers

[57] ABSTRACT

The present invention is a stabilized Romanowsky type stain solution. The stain solution which comprises azures, Methylene Blue and an eosin dye in methanol solution, is stabilized by the addition thereto of a stabilizing amount of a combination of dimethylamine hydrochloride and a second amine of the formula $R_2NH_2^+Cl^-$ or $R_3NH^+Cl^-$ where R is ethyl, n-propyl or n-butyl.

6 Claims, No Drawings

STABILIZED ROMANOWSKY STAIN SOLUTION

BACKGROUND OF THE INVENTION

This invention relates to blood staining systems and more particularly to the stabilization of Romanowsky type stains. Romanowsky type stains, e.g., Wright's solution and Giemsa's solution, comprise a methanol solution of Methylene Blue and an eosin dye along with other allied dyes. Typical allied dyes include Azure A, Azure B and Azure C.

In order to employ such a stain it is usually necessary to prepare a solution of the dry stain in methyl alcohol and apply the solution to a blood smear or the like. Next a buffer solution and a rinse solution are added stepwise to the stained smear until a visable physical change occurs.

The presence of a second dye in addition to Methylene Blue, particularly Eosin Y, is desirable to enhance the staining qualities of the solution. Other allied dyes, i.e., Azure A, Azure B and Azure C are also desirable for their enhancement of the solution's ability to stain the blood smear. The standard way of using the dye is to form the solution and allow it to stand for a period of time. The azure dyes in the stain powder are not very soluble in methanol. However, Methylene Blue degrades into azures in the presence of eosin upon aging in solution. It will normally take about two weeks of standing for optimal staining results to be achieved. Unfortunately, the dyes continue to oxidize, and the resultant oxidation products render the solution unsuitable for the intended purpose. Furthermore, random precipitation in the stain solution upon aging results in poor stain quality. Thus, while the stain solution takes about two weeks to become fully effective, it has a shelf life of only about 3 to approximately 12 months.

Gilliland et al disclose the use of HCl to stabilize a Romanowsky stain in Stain Technology, Vol. 54, No. 3, Pp. 141–150. The use of an acidic stain would, of course, be unsatisfactory in certain automated staining devices.

It is an object of the present invention to provide a non-acidic method for the stabilization of the above-described Romanowsky staining solutions.

It is a further object to provide a stabilized Romanowsky stain solution having a significantly increased shelf life.

SUMMARY OF THE INVENTION

The present invention is a Romanowsky type stain comprising azures, Methylene Blue and an eosin dye in methanol solution combined with a stabilizing amount of a combination of dimethylamine hydrochloride and a secondary or tertiary alkylamine hydrochloride of the formula $$R_2NH_2{}^+Cl^- \text{ or } R_3NH^+Cl^-$$

where R is ethyl, n-propyl or n-butyl.

DETAILED DESCRIPTION

The most widely used Romanowsky type stains are known as Wright's and Giemsa's solutions. Both comprise azures, Methylene Blue and an eosin dye in methanol solution; the former having an absorbance ratio of azures and Methylene Blue to eosin of about 1.70 to 2.10 with the latter having an absorbance ratio of about 1.70 to 1.80 (absorbance ratio equals $A_{650}/A_{525}$).

Reproducible stain performance, constant stain absorbance and absorbance ratios (as determined by spectrophotometer) and the absence of precipitates are indicators of a stable stain solution. The addition of dimethylamine hydrochloride to methanolic stain solutions was found to result in practically complete cessation of stain component degradation as evidenced by high performance liquid chromatography. However, this stain developed more precipitate than the control apparently due to the solubility of its additive cation -eosinate ion pair, and was, therefore, not an optimized composition. The addition of $R_2NH_2{}^+Cl^-$ or $R_3NH^+Cl^-$ (R=ethyl, n-propyl or n-butyl) to stain solutions was found to not only improve component stability but also to eliminate all stain precipitation problems under all conditions evaluated. However, these additives did not enhance component stability as fully as dimethylamine hydrochloride. It has now been discovered that the combination of these additives achieves both component stability and complete elimination of the precipitation problem. Of the additives which were found to prevent precipitation, $Et_2NH_2{}^+Cl^-$ was chosen for further study in combination with dimethylamine hydrochloride due to its commercial availability. The studies which illustrate the performance of this combination of additives in a Romanowsky type stain solution are described in the following examples:

EXAMPLE I

A solution was prepared by dissolving 3.0 grams (gm) of Wright's stain powder (MCB, Norwood, Ohio) in 100 milliliters (ml.) of methanol. The composition of the powder was 37% Eosin Y, 33% Methylene Blue and 30% azures and azure eosinate. After 20 minutes of shaking at room temperature and allowing the solution to stand for 2 weeks, undissolved powder was removed by filtration. The filtered stain solution was then diluted to 0.575 absorbance at 650 nanometers (nm.) (Beckman Spectrophotometer) before addition of the stabilizer.

Various concentrations of $Et_2NH_2{}^+Cl^-$ and $Me_2NH_2{}^+Cl^-$ together were studied: $Et_2NH_2{}^+Cl^-$ (0.5–0.7% by weight) and $Me_2NH_2{}^+Cl^-$ (0.05–0.2% by weight) were added to stain solutions.

For the purpose of stain shelf life prediction, stain solutions without additive were stressed at various temperatures for various periods up to 28 days. The absorbance ratio $(A_{650}/A_{525})$ of a stressed Wright's stain solution with or without the stabilizer of the present invention is set out in Table 1. These ratios were obtained by running the spectrophotometric scans of stain solutions after a 1/400 dilution. The ratio of absorbance of 650 nm to 525 nm (peak maximum at or near 525 nm) was designated for monitoring stability of the stain solutions. The ratio, designated herein as $r_A$ value, was found to decrease with the degradation of the stain. From Table 1 it can be determined that the stability of stain solutions was greatly improved with the addition of stabilizers especially at elevated temperatures.

TABLE 1

Absorbance Ratio ($r_A$) of Stressed Methanolic Wright's Stain Solutions
With the Addition of $Me_2NH_2{}^+Cl^-$ and $Et_2NH_2{}^+Cl^-$

| Temp. °C $r_A$ | 0% M 0% E | | | 0.2% M 0.6% E | | | 0.1% M 0.6% E | | | 0.05% M 0.6% E | | |
|---|---|---|---|---|---|---|---|---|---|---|---|---|
| Temp, Day | 23° | 40° | 50° | 23° | 40° | 50° | 23° | 40° | 50° | 23° | 40° | 50° |
| 0 | 1.68 | 1.68 | 1.68 | 1.68 | 1.68 | 1.68 | 1.68 | 1.68 | 1.68 | 1.68 | 1.68 | 1.68 |
| 6 | 1.63 | 1.49 | 1.29 | 1.71 | 1.68 | 1.67 | 1.67 | 1.67 | 1.64 | 1.67 | 1.66 | 1.61 |
| 14 | 1.62 | 1.36 | 1.16 | 1.69 | 1.67 | 1.64 | 1.75 | 1.71 | 1.66 | 1.68 | 1.63 | 1.56 |
| 28 | 1.60 | 1.26 | 0.84 | 1.72 | 1.68 | 1.64 | 1.69 | 1.62 | 1.59 | 1.66 | 1.57 | 1.47 |

EXAMPLE II

Differential staining performance of the solution, with and without the addition of both 0.6% $Et_2NH_2{}^+Cl^-$ and 0.1% $Me_2NH_2{}^+Cl^-$ was studied in this experiment. The control and stabilized solutions were tested for staining performance both before and after a 28 day stress period at 50° C. The results of this study are set out in Table 2.

TABLE 2

The Differential Staining Performance of Stain Solutions on Blood Smears With and Without the Addition of $Me_2NH_2{}^+Cl^-$ (M) and $Et_2NH_2{}^+Cl^-$ (E).

| Cell components Score* % Additive | Neutrophils | | Eosinophils | | Lymphocytes | | Monocytes | | Red Blood Cells | Platelets |
|---|---|---|---|---|---|---|---|---|---|---|
|  | N** | C** | N | C | N | C | N | C |  |  |
| A. Stain solutions before stress | | | | | | | | | | |
| 0% M 0% E | 4.4 ± 0.7 | 4.1 ± 0.8 | 4.1 ± 0.9 | 3.8 ± 0.5 | 4.5 ± 0.5 | 4.5 ± 0.5 | 4.5 ± 0.7 | 4.4 ± 0.7 | 4.1 ± 0.4 | 4.9 ± 0.2 |
| 0.1% M 0.6% E | 5.0 ± 0.0 | 4.8 ± 0.3 | 5.0 ± 0.0 | 4.7 ± 0.3 | 5.0 ± 0.0 | 5.0 ± 0.0 | 5.0 ± 0.0 | 5.0 ± 0.0 | 5.0 ± 0.0 | 4.9 ± 0.2 |
| B. Stain solutions after stress at 50° C. for 28 days | | | | | | | | | | |
| 0% M 0% E | 3.0 ± 0.4 | 2.4 ± 0.4 | 2.8 ± 0.5 | 3.9 ± 0.8 | 2.2 ± 0.5 | 2.2 ± 0.5 | 2.0 ± 0.0 | 2.2 ± 0.5 | 3.8 ± 0.5 | 2.7 ± 0.7 |
| 0.1% M 0.6% E | 5.0 ± 0.0 | 4.6 ± 0.4 | 5.0 ± 0.0 | 4.6 ± 0.4 | 5.0 ± 0.0 | 5.0 ± 0.0 | 4.8 ± 0.3 | 4.2 ± 0.3 | 4.2 ± 0.8 | 4.6 ± 0.9 |

*Average ± s (n = 5).
Score: 5, excellent; 4, good; 3, satisfactory and <3, not satisfactory
**N = nucleus;
C = cytoplasm From Table 2 it can be determined that performance before stress was slightly improved with the addition of the co-stabilizers suggesting that the stabilized stain penetrates cell membranes better than the unstabilized material. Performance of the control solution was unsatisfactory after a 28 day stress period at 50° C. while the co-stabilized stain continued to demonstrate good performance.

EXAMPLE III

This experiment was designed to enable one to predict the shelf life of a stain stabilized by the presently described system. All available evidence suggests that Methylene Blue (MB) and azures of Wright's stain continuously degrade in methanol at ambient temperature. Thus, the stain solution has a limited age during which satisfactory performance is obtained. To determine shelf life ages, stain solutions without stabilizer were stressed at 40° C. for various periods of time to produce a decay in $r_A$ values. Staining performance was evaluated at each checkpoint and solutions producing an $r_A \geq 1.0$ were determined to consistently provide satisfactory staining performance. Therefore, this minimum acceptable absorbance ratio was established for the prediction of stain shelf life.

Since stain shelf life is heavily dependent on the degradation of MB, the MB concentration of a stain solution was determined by high pressure liquid chromatography (HPLC). Plots of ln [MB] vs. age in days of a stain solution at elevated temperatures were linear indicating that the degradation of MB follows first order kinetics. Although accurate MB concentration in the stain solution can be obtained with HPLC, the $r_A$ value obtained from absorbance scans can also be applied to the prediction of stain shelf life. It was assumed that the absorbance of stain solution at 650 nm was primarily from MB. Therefore, decreases in $r_A$ value during aging reflect the loss of MB. Plots of ln ($r_A$) vs. age of stain solutions at various temperatures were also linear in the range of interest [ln($r_A$)>0]. The linear relationship, y=mx+b, of decayed $r_A$ values (y) and age (x) was used to calculate stain shelf life.

Table III shows predicted shelf lives of stain solutions with and without stabilizer. Two methods were used. First, the shelf life of stain solutions without stabilizer (control) and with the addition of 0.6% $Et_2NH_2{}^+Cl^-$ were calculated directly from the degradation slope at 23° C. using equation (1);

$$\text{Shelf life} = \frac{\ln(\text{minimum acceptable } r_A) - \ln(\text{initial } r_A)}{\text{Slope 23° C.}} \quad (1)$$

where minimum acceptable $r_A = 1.00$ and initial $r_A = 1.68$.

Second, shelf life of stain solutions with both 0.6% $Et_2NH_2{}^+Cl^-$ and 0.1% $Me_2NH_2{}^+Cl^-$ added were predicted indirectly. Such a stain solution is quite stable at room temperature but degrades slowly at 50° C. The degradation slope at 50° C., was obtained from plotting ln ($r_A$) vs. age of the stabilized stain solution. Since the rate of stain degradation was faster at elevated temperatures, the ratio of degradation rate of the control solution at elevated temperature to room temperature was calculated. The calculated ratio was 20 for the ratio of [Rate$_{50° C.}$/Rate$_{23° C.}$] and this calculated ratio was used for the prediction of degradation slope of co-stabilized stain solution at 23° C. The degradation slope at 23° C. of the co-stabilized stain solution was calculated using equation (2):

$$\text{Slope 23° C.} = \frac{\text{Slope}_{50° C.}}{[\text{Rate}_{50° C.}/\text{Rate}_{23° C.}]} \quad (2)$$

where slope$_{50° C.}$ was obtained from the co-stabilized solution and [Rate$_{50° C.}$/Rate$_{23° C.}$] was obtained from the corresponding control solution. The shelf life of the stain solution stabilized with Et$_2$NH$_2^+$Cl$^-$ and Me$_2$NH$_2^+$Cl$^-$ was then calculated with equation (1) using calculated slope$_{23° C.}$ obtained from equation (2).

The calculated shelf life of the control stain was 255 days or 0.7 years. This value was increased by 3.5 times with the addition of 0.6% Et$_2$NH$_2^+$Cl$^-$ and was increased approximately 27 times with the addition of both 0.6% Et$_2$NH$_2^+$Cl$^-$ and 0.1% Me$_2$NH$_2^+$Cl$^-$. The results of this experiment are summarized in Table III.

TABLE III

| Predicted Shelf Life of Stain Solutions | |
| --- | --- |
| Stabilizer in Stain Solution | Shelf Life, Years |
| Control (no stabilizer) | 0.7 |
| 0.6% Et$_2$NH$_2^+$Cl$^-$ | 2.5 |
| 0.1% Me$_2$NH$_2^+$Cl$^-$, 0.6% Et$_2$NH$_2^+$Cl$^-$ | 18.7 |

The amount of stabilizing additives to be added to the stain solution and their order of addition is not critical although the weight ratio of dimethylamine hydrochloride to the other stabilizer should be in the range of from about 1:10 to 1:3.5. The preferred amount of the combination of the two stabilizers will range from 0.55 to 0.9 weight percent of the stain solution which typically contains from 2 to 4 weight percent of the solid dyes dissolved in methanol.

The invention can be practiced as illustrated by the examples with other secondary or tertiary alkylamine hydrochlorides of the formula R$_2$NH$_2^+$Cl$^-$ or R$_3$NH$^+$Cl$^-$ such as dipropylamine hydrochloride, dibutylamine hydrochloride, tripropylamine hydrochloride and tributylamine hydrochloride in combination with dimethylamine hydrochloride.

What is claimed is:

1. A Romanowsky-type stain comprising azures, methylene blue and an eosin dye in methanol solution which contains from 0.55 to 0.9 weight percent of a combination of dimethylamine hydrochloride and a second stabilizer which is a secondary or tertiary alkylamine hydrochloride of the formula R$_2$NH$_2^+$Cl$^-$ or R$_3$NH$^+$Cl$^-$ where R is ethyl, n-propyl or n-butyl said dimethylamine hydrochloride and secondary or tertiary alkylamine hydrochloride being present in a ratio of dimethylamine hydrochloride to the other stabilizer in the range of from about 1:10 to 1:3.5.

2. The stain of claim 1 wherein the second stabilizer is a secondary alkylamine hydrochloride.

3. The stain of claim 2 wherein the secondary alkylamine hydrochloride is diethylamine hydrochloride.

4. The stain of claim 1 which comprises a methanol solution of a powder made up of 37% eosin Y, 33% methylene blue together with 30% azures and azure eosinate.

5. The stain of claim 1 wherein the stain solution contains from 2 to 4 weight percent of the solid dyes in solution.

6. A Romanowsky-type stain comprising 2 to 4 weight percent of a combination of azures, methylene blue and an eosin dye in methanol solution which contains from 0.55 to 0.9 weight percent of a combination of dimethylamine hydrochloride and diethylamine hydrochloride wherein the weight ratio of dimethylamine hydrochloride to diethylamine hydrochloride is in the range of from about 1:10 to 1:3.5.

* * * * *